United States Patent
Gebauer

(10) Patent No.: US 12,179,195 B2
(45) Date of Patent: Dec. 31, 2024

(54) BIOPROCESSING FLUID SENSOR ARRANGEMENT

(71) Applicant: Cytiva Sweden AB, Uppsala (SE)

(72) Inventor: Klaus Gebauer, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 56 days.

(21) Appl. No.: 17/281,727

(22) PCT Filed: Oct. 16, 2019

(86) PCT No.: PCT/EP2019/078122
§ 371 (c)(1),
(2) Date: Mar. 31, 2021

(87) PCT Pub. No.: WO2020/079101
PCT Pub. Date: Apr. 23, 2020

(65) Prior Publication Data
US 2021/0387189 A1  Dec. 16, 2021

(30) Foreign Application Priority Data
Oct. 17, 2018 (GB) ..................... 1816871

(51) Int. Cl.
*B01L 3/00* (2006.01)

(52) U.S. Cl.
CPC ... *B01L 3/502738* (2013.01); *B01L 2200/141* (2013.01); *B01L 2300/0663* (2013.01);
(Continued)

(58) Field of Classification Search
CPC ......... B01L 3/502738; B01L 2200/141; B01L 2300/0663; B01L 2300/0681; B01L 2400/0644; B01L 2400/0655; C12M 41/00
See application file for complete search history.

(56) References Cited

U.S. PATENT DOCUMENTS

2006/0277977 A1  12/2006  Kahn et al.
2012/0247234 A1  10/2012  Garrod et al.
(Continued)

FOREIGN PATENT DOCUMENTS

CN  205785303 U  12/2016
CN  112823061 A  5/2021
(Continued)

OTHER PUBLICATIONS

Chinese Office Action for CN Application No. 201980068483.X mailed May 20, 2022 (32 pages).
(Continued)

*Primary Examiner* — Samuel P Siefke
(74) *Attorney, Agent, or Firm* — Eversheds-Sutherland (US) LLP

(57) ABSTRACT

The present invention relates to a bioprocessing fluid sensor arrangement (100) for sensing fluidic properties in a process fluid path with a sensor (S), configured for aseptically connecting the sensor with at least one conditioning fluid while separating said sensor from the process fluid to at least one conditioning fluid e.g. for calibration, cleaning, regenerating and/or storing the sensor, the arrangement comprising a process fluid path (PF) having a process fluid inlet (PI) and a process fluid outlet (PO); a sensor (S) arranged in the process fluid path (PF); a bypass fluid path (BF) in the process fluid path (PF), for bypassing the sensor (S); a conditioning or cleaning fluid path (CF) having an inlet (CI) and an outlet (CO) each aseptically and fluidically connected to the process fluid path (PF), one on each side of the sensor (S); and flow controls (FC) for controlling the flow of fluids, whereby fluids can be controlled to flow either in the process fluid path (PF) via the sensor (S), or in the bypass fluid path (BF) omitting the sensor from the fluid path (PF), or in the conditioning or cleaning fluid path (CF) including the sensor (Continued)

in said flow but omitting the remaining process fluid path (PF) and bypass fluid path (BF).

15 Claims, 10 Drawing Sheets

(52) U.S. Cl.
CPC .................. *B01L 2300/0681* (2013.01); *B01L 2400/0644* (2013.01); *B01L 2400/0655* (2013.01)

(56) References Cited

U.S. PATENT DOCUMENTS

| | | | |
|---|---|---|---|
| 2013/0240065 | A1 | 9/2013 | Weissenbach et al. |
| 2018/0221823 | A1 | 8/2018 | Nutalapati et al. |

FOREIGN PATENT DOCUMENTS

| | | | |
|---|---|---|---|
| EP | 1542000 | A | 6/2005 |
| GB | 1602151 | A | 11/1981 |
| JP | H08334463 | A1 | 12/1996 |
| JP | 2004125777 | A | 4/2004 |
| JP | 2012213772 | A | 11/2012 |
| JP | 2013530754 | A | 8/2013 |
| JP | 2018525219 | A | 9/2018 |
| JP | 2019535260 | A | 12/2019 |
| WO | 2004011925 | A1 | 2/2004 |
| WO | 2016/116535 | A1 | 7/2016 |
| WO | 2018086997 | A1 | 5/2018 |
| WO | 2018158273 | A1 | 9/2018 |

OTHER PUBLICATIONS

PCT International Search Report and Written Opinion for PCT/EP2019/078122 mailed Mar. 12, 2020 (20 pages).
Great Britain Search Report for GB Application No. 18166871.6 mailed Apr. 18, 2019 (3 pages).
Office Action Issued in Chinese Patent Application No. 201980068483.X, dated Jan. 5, 2023, with English Summary (30 Pages).
Japanese Notice of Allowance issued in corresponding JP Patent Application No. 2021-520394, dated Jul. 8, 2024, (4 pages).

BIOPROCESSING FLUID SENSOR ARRANGEMENT

CROSS REFERENCE TO RELATED APPLICATIONS

This application claims the priority benefit of PCT/EP2019/078122, filed on Oct. 16, 2019, which claims the benefit of Great Britain Application No. 1816871.6, filed on Oct. 17, 2018, the entire contents of which are incorporated by reference herein.

TECHNICAL FIELD

The present invention relates to a bioprocessing fluid sensor arrangement for sensing fluidic properties in a process fluid path and further configured for aseptic sensor connection to additional conditioning or cleaning or bypass paths. The invention further relates to a sensor unit, a bioprocessing sensor system and method thereof.

BACKGROUND

The biotechnology industry, frequently use continuous bioprocessing systems operating over longer time. In such systems, there is a need for periodic conditioning such as calibration of sensors, cleaning of sensors or fluid paths, regeneration and/or storing/replacement of the sensors. It is then important to avoid contamination and/or loss of sterility during such a conditioning event.

In one example, during a typical bioprocessing manufacturing process, there is typically a need to incorporate sensors into the manufacturing process so that process properties/variables are monitored in the process fluid. For example, the process properties/variables that need to be monitored may include temperature, pressure, pH, conductivity, and the like. In conventional setups, sensors are placed directly along one or more points of the production process whereby the sensors themselves are inserted into the process fluid path where the sensor makes direct contact with the process fluid. In conventional manufacturing processes, the sensors may need to be changed, for example, due to a malfunction or because the product being manufactured requires a different sensor. In these examples, it can be a time consuming and expensive process to replace these sensors and also ensuring that the process fluid remain uncontaminated.

Some conventional systems use controlled environments such as clean rooms or cabinets to ensure aseptic conditions. When necessary connections are made in such a controlled environment that breaches sterile tubing and piping, the environment does not contaminate the fluid flow passage. However, maintaining a clean room is time consuming, difficult and costly to validate.

There is therefore a need for an improved bioprocessing fluid sensor arrangement, bioprocessing sensor unit, bioprocessing sensor system and method therefore.

OBJECTS OF THE INVENTION

An objective of embodiments of the present invention is to provide a solution which mitigates or solves the drawbacks and problems described above.

SUMMARY OF THE INVENTION

The above objective is achieved by the subject matter described herein. Further advantageous implementation forms of the invention are further defined herein According to a first aspect of the invention, the above mentioned and other objectives are achieved by a bioprocessing fluid sensor arrangement for sensing fluidic properties in a process fluid path with a sensor, configured for aseptically connecting the sensor with at least one conditioning fluid while separating said sensor from the process fluid to at least one conditioning fluid e.g. for calibration, cleaning, regenerating and/or storing the sensor, the arrangement comprising a process fluid path having a process fluid inlet and a process fluid outlet; a sensor arranged in the process fluid path; a bypass fluid path in the process fluid path, for bypassing the sensor; a conditioning or cleaning fluid path having an inlet and an outlet each aseptically and fluidically connected to the process fluid path, one on each side of the sensor; and flow controls for controlling the flow of fluids, whereby fluids can be controlled to flow either in the process fluid path via the sensor, or in the bypass fluid path omitting the sensor from the fluid path, or in the conditioning or cleaning fluid path including the sensor in said flow but omitting the remaining process fluid path and bypass fluid path.

An advantage of the embodiment according to the first aspect is that the risk of contamination is reduced.

According to a second aspect of the invention, the above mentioned and other objectives are achieved by a bioprocessing fluid sensor unit.

According to a third aspect of the invention, the above mentioned and other objectives are achieved by a bioprocessing sensor system.

According to a fourth aspect of the invention, the above mentioned and other objectives are achieved by method performed by the bioprocessing sensor system.

The advantages of the second, third and fourth aspects are at least the same as for the first aspect.

Further applications and advantages of embodiments of the invention will be apparent from the following detailed description.

Figure 1:
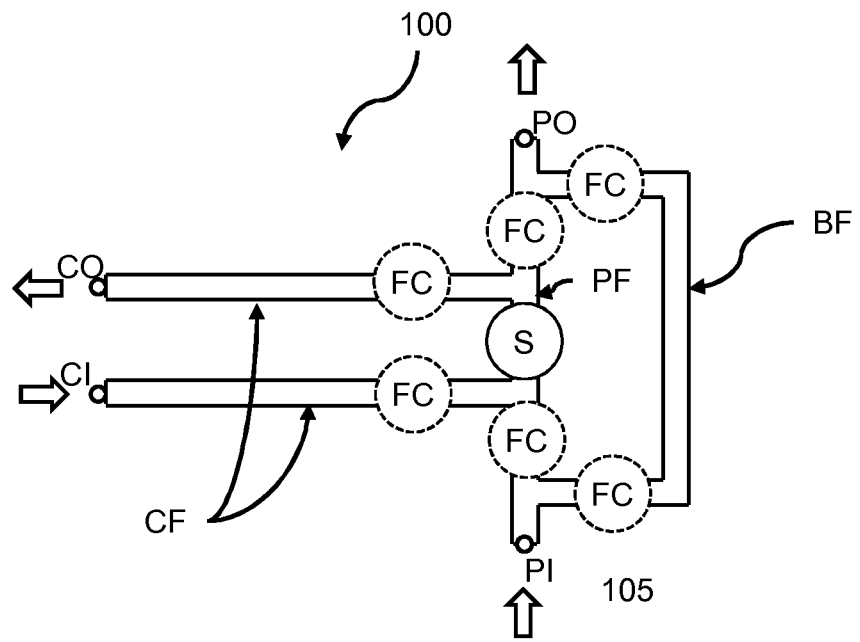
FIG. 1 shows a bioprocessing fluid sensor arrangement according to one or more embodiments of the present disclosure.

A more complete understanding of embodiments of the invention will be afforded to those skilled in the art, as well as a realization of additional advantages thereof, by a consideration of the following detailed description of one or

DETAILED DESCRIPTION

An "or" in this description and the corresponding claims is to be understood as a mathematical OR which covers "and" and "or", and is not to be understand as an XOR (exclusive OR). The indefinite article "a" in this disclosure and claims is not limited to "one" and can also be understood as "one or more", i.e., plural.

In the present disclosure the term "fluid path" denotes an arrangement for conveying a fluid. The fluid path typically comprises one or more conduits connecting fluid inlets and fluid outlets and any intermediate components/equipment, such as filters, ventilators, sensors valves etc.

In the present disclosure the terms "connector"/"coupler" (used interchangeably herein) denote an arrangement configured to close off a fluid path and thereby protect a sensor arrangement and/or a sensor unit and/or the operator and/or environment from contamination or exposure to hazardous substances. Alternatively, such a connector/coupler may be configured to provide aseptic connectivity. In other words, configured to provide strict and complete closure of the fluid paths, when not connected. When using aseptic connectors/couplers or disconnectors, sterility of a fluid path, two connected fluid paths or components, or two disconnected lines or components can be maintained, provided that the fluid paths or components involved in the operation have been provided sterile. With these features a sensor arrangement or sensor unit allows not only for more efficient bioprocessing, it may also allow for reducing requirements on classification and containment of facilities, thereby reducing cost and risk for contamination or infection of the process fluid and drug product, and/or contamination and infection of the process environment, facility or the operator.

In one embodiment, the disclosure is described for a typical multi-use bioprocessing system or a combined/hybrid multi-use bioprocessing system and single-use bioprocessing system. Fluid inlets and fluid outlets are connected by one or more conduits and intermediate components/equipment forming a fluid path from the separate conduits and intermediate components/equipment.

The multi-use system may in one example be a traditional system, for example a stainless steel system, that may be pre-sterilized by steam sterilization, for example Steaming in Place (SIP) or autoclaving. This system may be connected aseptically with single-use system parts or other parts, such as for example sensors, that have been pre-sterilized by other means.

Hereby, a hybrid system is formed, and pre-sterilized components typically described as single-use components or consumables may be utilized also over longer periods of time, especially when allowing condition of the single-use components, for example a sensor, as described by the present invention disclosure.

In further embodiments herein, the present disclosure is directed to hybrid systems, characterized by a mix and/or combination between single-use technology, systems, subsystems or components and traditional systems, subsystems or components.

FIG. 1 shows a bioprocessing fluid sensor arrangement 100 according to one or more embodiments of the present disclosure. In one embodiment, the sensor arrangement 100 is a conventional sensor configured for sensing fluidic properties in a process fluid path using a sensor S. The arrangement is also configured for aseptically connecting the sensor S with at least one conditioning fluid while separating said sensor from the process for calibration, cleaning, regenerating and/or storing in readiness for use the sensor. In one embodiment, the sensor arrangement 100 is configured for sensing fluidic properties in a process fluid path and further configured for aseptic sensor S connection to additional calibration, or cleaning or bypass fluid paths.

The sensor arrangement 100, comprises a process fluid path PF having a process fluid inlet PI and a process fluid outlet PO. The process fluid path PF may further comprise one or more conduits coupling or connecting the process fluid inlet PI and the process fluid outlet PO. The sensor arrangement 100, further comprises a sensor S arranged in the process fluid path PF. The process fluid path PF may further comprise one or more conduits coupling or connecting the sensor S to the process fluid inlet PI and to the process fluid outlet PO. The fluid inlet PI and the process fluid outlet PO may further comprise process couplers and configured to provide aseptic connection of the sensor arrangement 100 to other bioprocessing units/components via the process fluid inlet PI and the process fluid outlet PO of the sensor arrangement 100.

The process couplers may e.g. be any of ReadyMate couplers (GE Healthcare), AseptiQuik (Colder Products), and Kleenpak, (Pall). Examples for aseptic couplers supporting multiple aseptic connections and disconnections are Lynx connectors (Millipore).

The sensor arrangement 100 further comprises a bypass path BF in or aseptically and fluidically connected to the process fluid path PF, suitable for or adapted to bypass the sensor S. The bypass path BF may further comprise one or more conduits coupling or connecting an inlet of the sensor to an outlet of the sensor, e.g. by connecting or coupling the fluid inlet PI to the process fluid outlet PO.

The sensor arrangement 100 further comprises a conditioning or cleaning fluid path CF having a conditioning or cleaning fluid inlet CI and a conditioning or cleaning fluid outlet CO, each aseptically and fluidically connected to the process fluid path PF, one on each side of the sensor S, e.g. an inlet of the sensor to an outlet of the sensor.

The conditioning fluid inlet CI and the conditioning fluid outlet CO may further comprise couplers and configured to provide aseptic connection of the sensor arrangement 100 to other bioprocessing units/components via the conditioning fluid inlet CI and the conditioning fluid outlet CO of the sensor arrangement 100. The couplers may e.g. be any of ReadyMate couplers (GE Healthcare), AseptiQuik (Colder Products), and Kleenpak, (Pall). Examples for aseptic couplers supporting multiple aseptic connections and disconnections are Lynx connectors (Millipore).

The conditioning or cleaning fluid path CF may further comprise one or more conduits coupling or connecting the cleaning fluid inlet CI to the inlet of the sensor and the conditioning or cleaning fluid outlet CO to an outlet of the sensor.

The sensor arrangement 100, further comprises one or more flow controls FC for controlling the flow of fluids, whereby fluids can be controlled to flow either in the process fluid path PF via the sensor S, or in the bypass path BF omitting the sensor from the fluid path PF, or in the conditioning or cleaning fluid path CF including the sensor in said flow but omitting the remaining process fluid path PF and bypass path BF. The flow controls FC are further described in FIG. 3-7. The conduits described above may comprise any material compatible with the bioprocess. Materials compatible with bioprocesses and biopharmaceutical production are classified for compatibility and suitability for parenteral drugs to avoid adverse impact on the drug substance, drug product and patient. Typically, certifications and full traceability is required for all wetted parts, for example in regard to compliance with USP (United States Pharmacopeia) or ISO standards such as for example USP VI, USP 88/87, CFR177 and animal free origin (AFO).

In one or more embodiments, the disclosure is directed to single use. The sensor S may be comprised in a body as a sensor unit, which may be disposed, e.g. after the bioprocess is completed.

Single-use technology (SUT) is a recent development addressing needs to reduce production cost, increase production throughput and quality and to increase safety in bioprocessing/bio-manufacturing. With single-use processing technology and components/equipment, wetted parts that are in contact with the process fluid and drug product during processing, such as for example fluid storage vessels, tubing, separation components/equipment etc., are provided as clean and ready to use consumables which are to be installed and used for a specific process, product or over a limited time only and to be disposed thereafter.

SUT consumables are typically produced, configured and packaged in clean room environments to avoid contamination with microorganisms, particulates etc. SUT wetted parts can further be provided clean and pre-sterilized, thus allowing for aseptic and/or sterile processing, hereby reducing above mentioned risks relevant for product, operator or patient safety. Typically, SUT wetted parts are subjected to a sterilizing gramma irradiation treatment prior to use in the biomanufacturing process, and when doing so they are deployed as 'pre-sterilized' at the point of use. This may involve providing the consumable with a formal and validated sterile claim after the sterilizing treatment, however, it may involve to alternatively providing a consumable that has undergone a sterilizing treatment but is provided without a formal sterile claim. With controlled and rigorous manufacturing conditions, SUT consumables may also be deployed non-sterile and/or with treatments that controls the state and condition of the consumable. Hereby, contamination levels by microorganisms, generally called 'bioburden', or levels of contamination or presence of contaminating substances or particles may be controlled and maintained within pre-defined levels.

Figure 2:
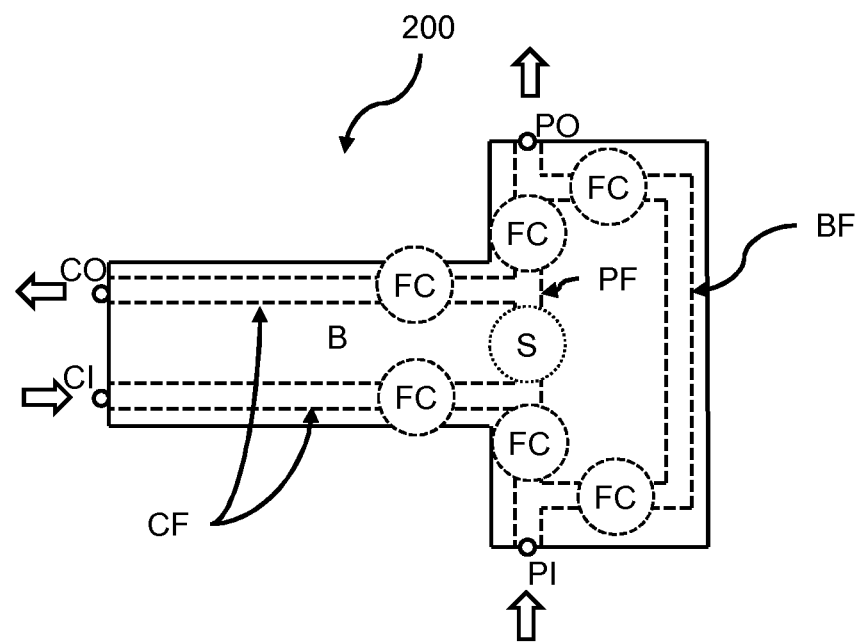
FIG. 2 shows a bioprocessing fluid sensor unit according to one or more embodiments of the present disclosure.

FIG. 2 shows a bioprocessing fluid sensor unit 200 according to one or more embodiments of the present disclosure. In one embodiment, the fluid sensor unit 200 is a conventional sensor configured for sensing fluidic properties in a process fluid path with a sensor S and for aseptically connecting the sensor with at least one conditioning fluid while separating said sensor from the process fluid, for calibration, cleaning, regenerating and/or storing ready for use the sensor. In one embodiment, the sensor arrangement 100 is configured for sensing fluidic properties in a process fluid path and further configured for aseptic sensor S connection to additional calibration, or cleaning or bypass fluid paths. The fluid sensor unit 200 comprising a body B. The body B may comprise any material compatible with the bioprocess, such as plastic or metal. Materials compatible with bioprocesses and biopharmaceutical production are classified for compatibility and suitability for parenteral drugs to avoid adverse impact on the drug substance, drug product and patient. Typically, certifications and full traceability is required for all wetted parts, for example in regard to compliance with USP (United States Pharmacopeia) or ISO standards such as for example USP VI, USP 88/87, CFR177 and animal free origin (AFO).

The sensor unit 200 may further comprise a process fluid inlet PI and a process fluid outlet PO. The process fluid inlet PI and the process fluid outlet PO may each be aseptically and fluidically connected to a process fluid path PF. The sensor unit 200 further may comprise process couplers, e.g. coupled to the body B, and configured to provide aseptic connection via the process fluid inlet PI and the process fluid outlet PO. The process couplers may be any suitable process couplers. The process couplers may e.g. be any of ReadyMate couplers (GE Healthcare), AseptiQuik (Colder Products), and Kleenpak, (Pall). Examples for aseptic couplers supporting multiple aseptic connections and disconnections are Lynx connectors (Millipore).

The sensor unit 200 may further comprise a conditioning fluid inlet CI and a conditioning fluid outlet CO. The conditioning fluid inlet CI and the conditioning fluid outlet CO may each be aseptically and fluidically connected to a process fluid path CF, one to each side of the sensor S, e.g. to an inlet of the sensor and to an outlet of the sensor S.

The conditioning fluid inlet CI and the conditioning fluid outlet CO may further comprise couplers, optionally attached to or integrated into the body B, and configured to provide aseptic connection of the sensor unit 200 to other bioprocessing units/components via the conditioning fluid inlet CI and the conditioning fluid outlet CO of the sensor unit 200. The couplers may e.g. be any of ReadyMate couplers (GE Healthcare), AseptiQuik (Colder Products), and Kleenpak, (Pall). Examples for aseptic couplers supporting multiple aseptic connections and disconnections are Lynx connectors (Millipore).

The conditioning path CF may further comprise one or more conduits coupling or connecting the conditioning fluid inlet CI to the inlet of the sensor and the conditioning fluid outlet PO to an outlet of the sensor.

The sensor unit 200 may further comprise a bypass path BF aseptically and fluidically connected to the process fluid path CF, one end to each of the sides of the sensor S. The bypass path BF may further comprise one or more conduits coupling or connecting the the inlet of the sensor S to the outlet of the sensor S.

The conduits described above may comprise any material compatible with the bioprocess. Materials compatible with bioprocesses and biopharmaceutical production are classified for compatibility and suitability for parenteral drugs to avoid adverse impact on the drug substance, drug product and patient. Typically, certifications and full traceability is required for all wetted parts, for example in regard to compliance with USP (United States Pharmacopeia) or ISO standards such as for example USP VI, USP 88/87, CFR177 and animal free origin (AFO).

The sensor unit 200 further may comprise an internal coupling network comprising the fluid paths PF, BF, CF and one or more flow controls FC for controlling the flow of fluids in the fluid paths PF, BF, CF. The flow controls FC may e.g. be manual valves or valves controllable by a control signal, e.g. electric or pneumatic valves.

The coupling network is configured to operate in an operational mode, where the flow controls FC of the internal coupling network are configured to allow fluid to flow from the process fluid inlet PI to the process fluid outlet PO via the sensor S. Alternatively or additionally, the coupling network is configured to operate in a conditioning mode, where the flow controls FC of the internal coupling network are configured to allow fluid to flow from the conditioning fluid inlet CI to the conditioning fluid outlet CO via the sensor S or to flow from the calibration fluid inlet CI to the fluid outlet PO via the sensor S.

In one example, the flow controls FC comprises one or more manual valves operated by a common control, such as a lever or dial. When the common control is set to a position indicating an operational mode, the manual valves of the internal coupling network are moved to a position which allows fluid to flow from the process fluid inlet PI to the process fluid outlet PO via the sensor S. When the common control is set to a position indicating an conditioning mode, the manual valves of the internal coupling network are moved to a position which allows fluid to flow from the conditioning fluid inlet CI to the conditioning fluid outlet CO via the sensor S or to flow from the calibration fluid inlet CI to the fluid outlet PO via the sensor S.

In one example, the flow controls FC comprises one or more valves controllable by a control signal, typically received from a control unit CU or an input device 917, such as a switch. When the control signals are indicative of an operational mode, the controllable valves of the internal coupling network are moved to a position which allows fluid to flow from the process fluid inlet PI to the process fluid outlet PO via the sensor S. When the control signals are indicative of an conditioning mode, the controllable valves of the internal coupling network are moved to a position which allows fluid to flow from the conditioning fluid inlet CI to the conditioning fluid outlet CO via the sensor S or to flow from the calibration fluid inlet CI to the fluid outlet PO via the sensor S.

In one embodiment of the invention, the flow controls FC may comprise diaphragm valves or pinch valves as flow controls.

In other embodiments of the invention, the flow controls FC may comprise one or more rotary valves as flow controls.

In further embodiments of the invention, the flow controls FC may comprise lever valves.

Rotary valves or lever valves may provide advantages with coordinating or incorporating multiple flow controls with fewer actuations required, for example closing one or more fluid paths while at the same time opening one or more fluid paths when turning the rotor of a rotary valve, for example.

In one embodiment, the sensor unit 200 is configured for single-use technology, SUT, usage. E.g. comprising or made out of plastic materials that can be disposed of after use for a single drug product only.

This embodiment has at least the advantage that that cross-contamination in between production batches and campaigns are reduced and/or eliminated. The advantage of using single-use technology (SUT) fluid handling equipment is primarily that cross-contamination in between production batches and campaigns is eliminated when the SUT equipment is used for a single drug product only. The SUT equipment is disposed of after use, which can be after a single run, batch or campaign comprising multiple runs and batches. When providing SUT equipment pre-sterilized or by other means bioburden controlled, initial cleaning and sanitization (for example by contacting the flow path with sodium hydroxide solutions) or sterilization can be avoided. This enables a LEAN manufacturing approach, because time consuming, costly and non-value adding steps can be omitted. When using the SUT for a single run or batch only, even cleaning post-use may be omitted. The elimination of cleaning procedures and required cleaning fluids further reduces clean water requirements to prepare cleaning solutions in the first place, fluid handling and waste treatment, which translates to reduced facility size and complexity.

Single-use equipment may be provided with fluid connectors that enable closed processing and thereby protect the process fluid line and/or the operator and environment from contamination or exposure to hazardous substances. Alternatively, fluid connectors may be providing aseptic connectivity features, hereby providing strict and complete closure of the fluid lines. When using aseptic connectors or disconnectors, sterility of a fluid line, two connected lines or components, or two disconnected lines or components can be maintained, provided that the fluid lines or components involved in the operation have been provided sterile. With these features, SUT equipment allows not only for more efficient processing, it may also allow for reducing requirements on classification and containment of facilities, thereby reducing cost and risk for contamination or infection of the process fluid and drug product, and/or contamination and infection of the process environment, facility or the operator.

SUT systems provide higher flexibility in (re-)configuring a manufacturing facility and adapting it to different processes and products by design, i.e. through the reduced need for fixed installations compared to traditional processing systems and installations, which for example required auxiliary systems for CIP and SIP. Nowadays, SUT equipment and SUT processing regimes are therefore available or are being made available for the majority of all types of equipment and/or unit operations, among them bioreactors for cell culture or fermentation, buffer bags for liquid storage, tubing and pumps for liquid transfer and filling operations, filters, chromatography columns and related systems for separations.

With these features, SUT equipment does provide improved efficiency, safety and convenience compared to traditional installations and systems. Traditional installations and systems for processing are typically made from stainless steel and/or plastic and are not produced under controlled (or clean room) conditions reducing bioburden. Traditional systems are typically cleaned in place (CIP), sometimes also sterilized in place (SIP), which not only requires auxiliary installations, equipment and fluids, but involves also substantial time for validation, execution, and quality control of CIP and SIP procedures. The size, cost and complexity of facilities relying on traditional equipment and installations is significantly larger compared to production facilities deploying SUT. SUT facilities and processes can be planned, built and started up in significantly shorter time compared to traditional manufacturing technology, and SUT reduces capital investments and financial risk associated with a typically highly dynamic portfolio of drug products as well as risk and uncertainty related to the testing and approval of drug candidates and their product demand.

Figure 3A:
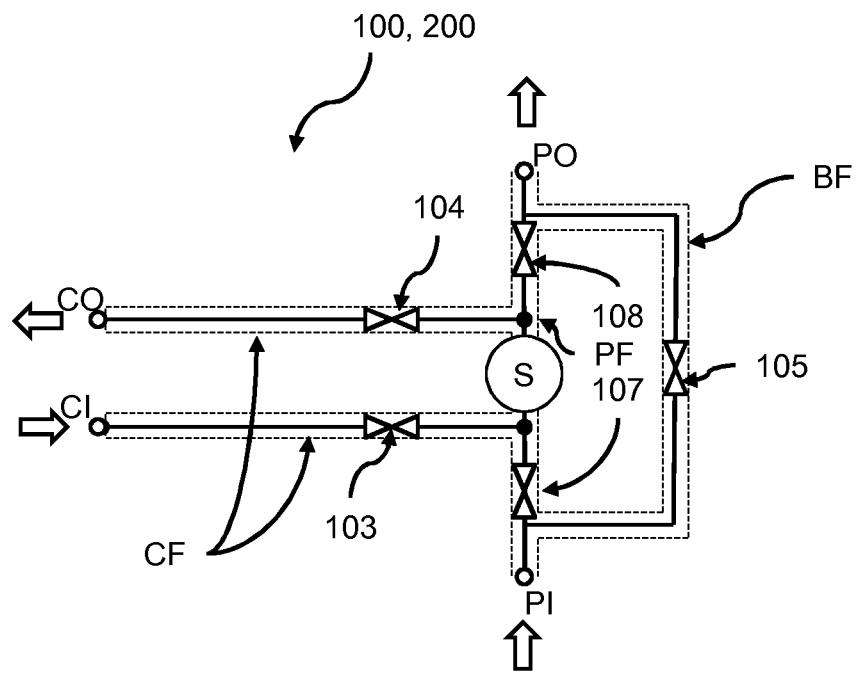
FIGS. 3a and 3b shows an embodiment of fluid paths according to one or more embodiments of the present disclosure.

FIG. 3A shows an embodiment of fluid paths according to one or more embodiments of the present disclosure. In one embodiment, the fluid paths PF, BF, CF are comprised in the fluid sensor arrangement 100 and/or the bioprocessing sensor unit 200. In one embodiment, the bypass path BF comprises a single bypass inlet valve 105 coupled to the process fluid inlet PI and an inlet of the sensor S.

Figure 3B:
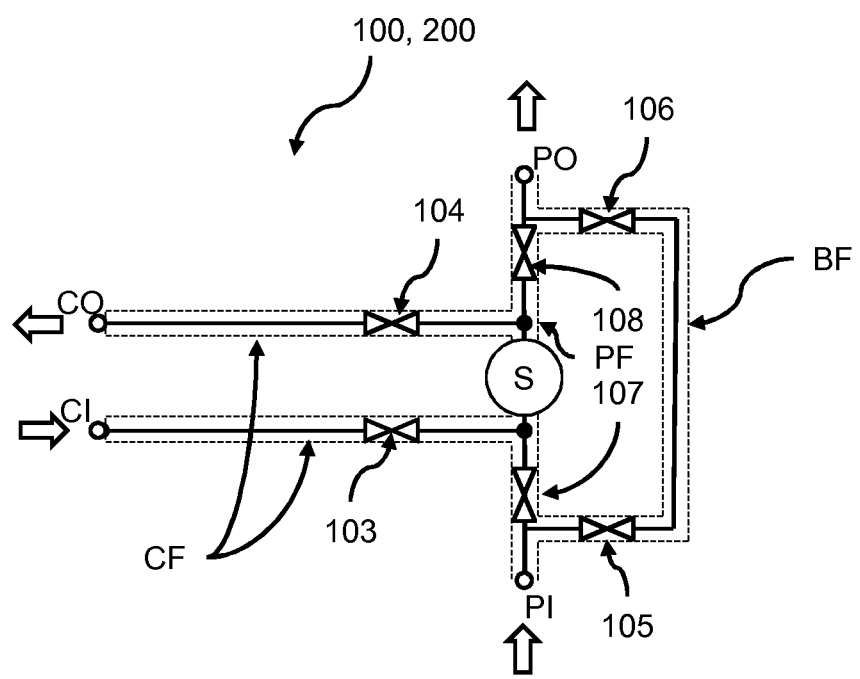

FIG. 3B shows an embodiment of fluid paths according to one or more embodiments of the present disclosure. In one embodiment, the fluid paths PF, BF, CF are comprised in the fluid sensor arrangement 100 and/or the bioprocessing sensor unit 200. In one embodiment, the bypass path BF comprises a bypass inlet valve 105 coupled to the process fluid inlet PI and an inlet of the sensor S and a bypass outlet valve 106 coupled to an outlet of the first sensor S and the process fluid outlet PO.

In any of the embodiments described in relation to FIG. 3A or 3B, the process fluid path PF comprises flow controls FC in the form of a process fluid inlet valve 107 coupled between the process fluid inlet PI and the inlet of the first sensor S and/or a process fluid outlet valve 108 coupled between an outlet of the first sensor S and the process fluid outlet PO. It is understood that one or both of the valves 107, 108 may be included depending on the application.

In any of the embodiments described in relation to FIG. 3A or 3B, the bypass path BF may comprises at least one flow control in the form of a bypass inlet valve 105 coupled to the process fluid inlet PI and an inlet of the sensor S and/or a bypass outlet valve 106 coupled between an outlet of the first sensor S and the process fluid outlet PO.

In any of the embodiments described in relation to FIG. 3A or 3B, the conditioning or cleaning fluid path CF comprises flow controls in the form of a conditioning fluid inlet valve 103 and/or a conditioning fluid outlet valve 104. It is understood that one or both of the valves 107, 108 may be included depending on the application.

In any of the embodiments described in relation to FIG. 3A or 3B, the conditioning fluid inlet valve 103 and/or conditioning fluid outlet valve 104 and/or the bypass inlet valve 105 and/or the bypass outlet valve 106 are configured to stop fluid to flow through the valves or to allow fluid to flow through the valves. The process fluid inlet valve 107 and/or the process fluid outlet valve 108 are simultaneously configured to allow fluid to flow through the valves or configured to stop fluid to flow through the valves.

In any of the embodiments described in relation to FIG. 3A or 3B, the conditioning fluid inlet valve 103 and/or the conditioning fluid outlet valve 104 and/or the bypass inlet valve 105 and/or the bypass outlet valve 106 are configured to stop fluid to flow through the valves in an operational mode or to allow fluid to flow through the valves in a conditioning mode. The process fluid inlet valve 107 and/or the process fluid outlet valve 108 are simultaneously configured to allow fluid to flow through the valves in the operational mode or configured to stop fluid to flow through the valves in the conditioning mode.

In some situations, it is desirable to have a configuration with reduced complexity. An embodiment with a reduced complexity is shown in FIG. 4.

Figure 4:
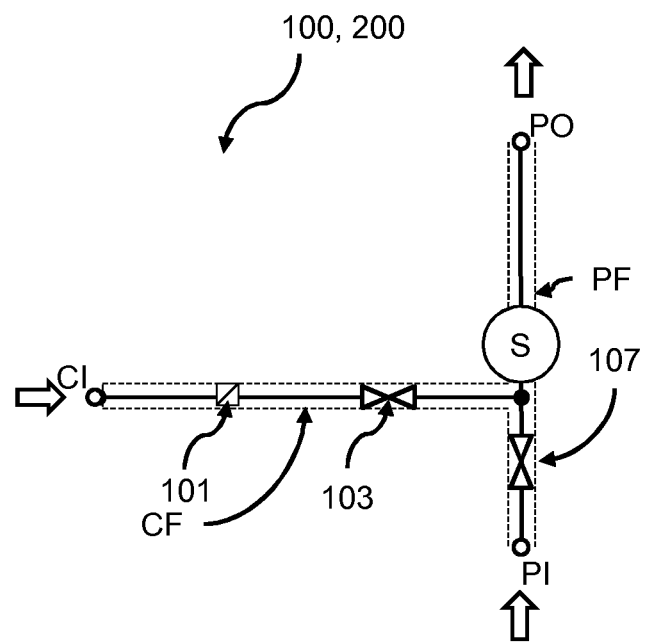
FIG. 4 shows yet an embodiment of fluid paths according to one or more embodiments of the present disclosure.

FIG. 4 shows yet an embodiment of fluid paths according to one or more embodiments of the present disclosure.

In one embodiment, the fluid paths PF, BF, CF are comprised in the fluid sensor arrangement 100 or in the sensor unit 200.

In this embodiment, the process fluid path PF comprises flow controls in the form of a process fluid inlet valve 107 coupled between the process fluid inlet PI and the inlet of the first sensor S.

In this embodiment, the conditioning fluid path CF comprises flow controls in the form of a conditioning fluid inlet valve 103. The conditioning fluid path CF may optionally further comprise a first sterile filter 101.

In one embodiment, the conditioning fluid inlet valve 103, is configured to stop fluid to flow through the valve or to allow fluid to flow through the valve. The process fluid inlet valve 107 is configured to allow fluid to flow through the valve or configured to stop fluid to flow through the valve.

In one embodiment, the conditioning fluid inlet valve 103 is configured to stop fluid to flow through the valve in the operational mode and configured to allow fluid to flow through the valve in the conditioning mode. The process fluid inlet valve 107 is configured to allow fluid to flow through the valve in the operational mode and configured to stop fluid to flow through the valve in the conditioning mode.

In some situations, it may be desirable to continue making measurements of process properties/variables using the sensor also during a conditioning event. In some embodiments of the present disclosure, this is achieved by providing a second sensor $S_c$.

This embodiment has the further advantage that conditioning can be performed with reduced complexity.

Figure 5:
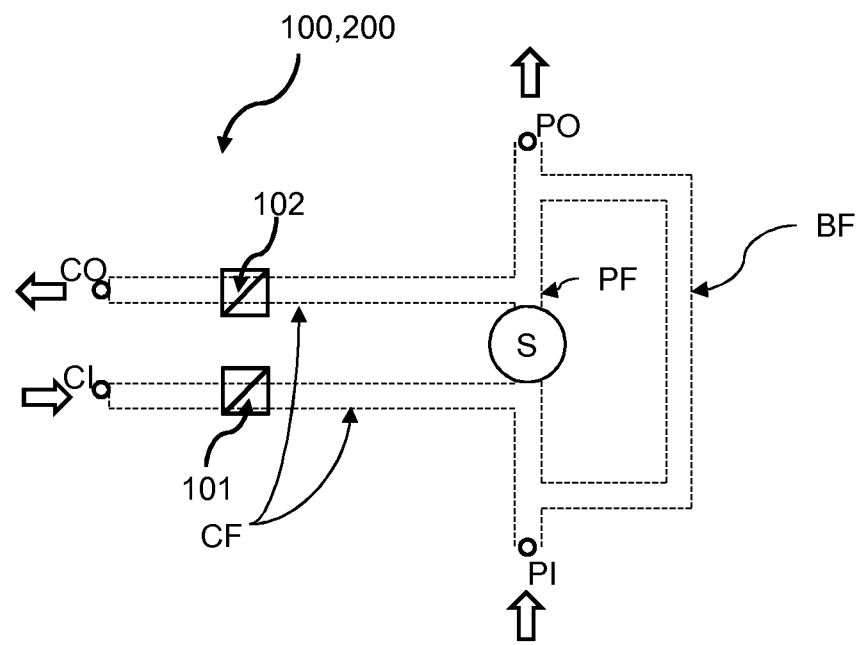
FIG. 5 shows an embodiment with a sterile filters according to one or more embodiments of the present disclosure.

FIG. 5 shows an embodiment with sterile filters according to one or more embodiments of the present disclosure. In one embodiment, the fluid paths PF, BF, CF are comprised in the fluid sensor arrangement 100 or in the sensor unit 200. The conditioning fluid path CF further comprises a first sterile filter 101 and/or a second sterile filter (102).

In one embodiment (not shown), conditioning fluid(s) with its supplying and receiving vessels and other optional components (e.g. pump(s) or valve(s)) may be aseptically connected to CI or CO or may be already pre-connected and supplied with the sensor arrangement 100 and/or sensor unit 200.

Figure 6A:
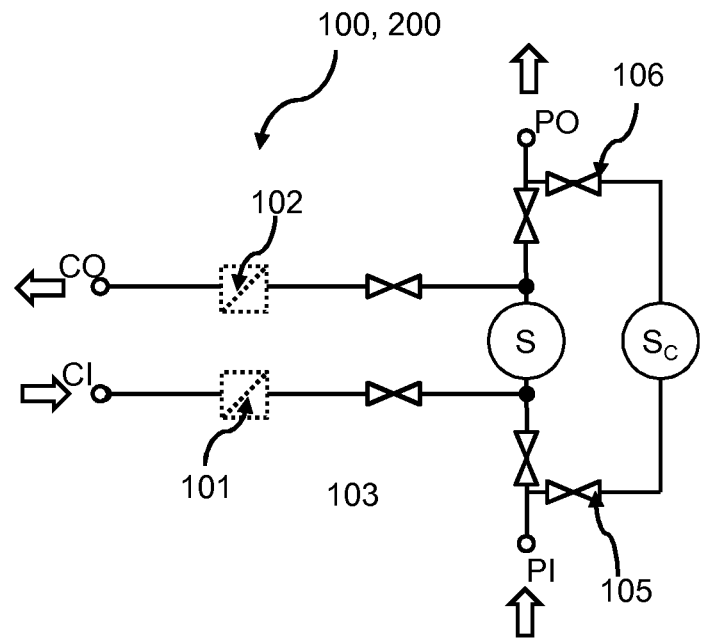
FIGS. 6A and 6B shows embodiments with a second sensor according to one or more embodiments of the present disclosure.

This embodiment has the further advantage that the risk of contamination is further reduced FIG. 6A shows an embodiment with a second conventional sensor according to one or more embodiments of the present disclosure. In one embodiment, the fluid paths PF, BF, CF are comprised in the fluid sensor arrangement 100 or in the sensor unit 200. In one embodiment, the fluid sensor arrangement 100 or the sensor unit 200 comprises a second sensor $S_c$, the second sensor $S_c$ being arranged in the bypass path BF. This embodiment has at least the advantage that measurements can be obtained continuously by alternatively receiving measurements from the sensor S and/or from the second sensor $S_c$.

Figure 6B:
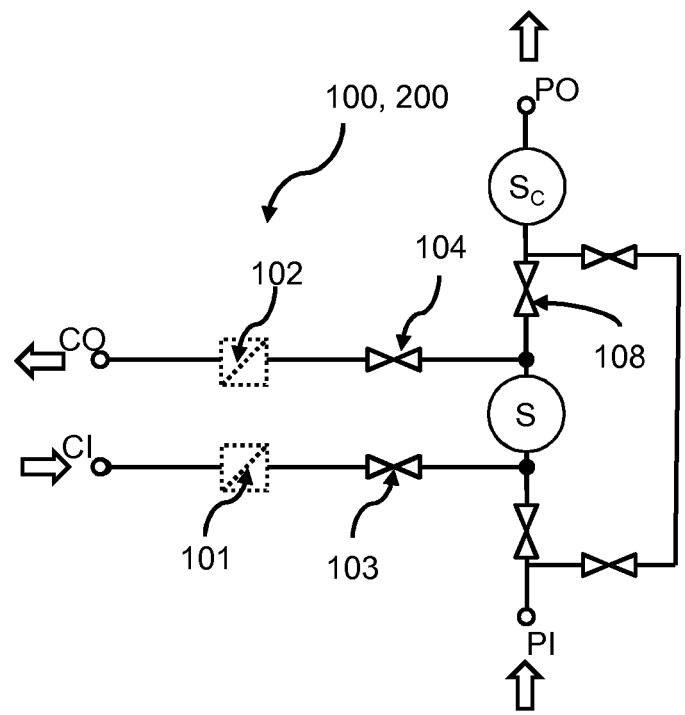

FIG. 6B shows an embodiment with another second conventional sensor according to one or more embodiments of the present disclosure. In one embodiment, the fluid paths PF, BF, CF are comprised in the fluid sensor arrangement 100 or in the sensor unit 200. In one embodiment, the fluid sensor arrangement 100 or the sensor unit 200 comprises a second sensor $S_c$, the second sensor $S_c$ being arranged in the process fluid PF path. This embodiment has at least the advantage that measurements can be obtained continuously by alternatively receiving measurements from the sensor S and/or from the second sensor $S_c$.

These embodiments have the further advantage that measurements may be performed continuously both when conditioning is performed and when it is not. The skilled addressee would realise that the second sensors of FIGS. 6A and 6B, could, in addition to the fluid circuits shown, have their own conditioning circuit CI, CO. Also the sensor $S_c$ shown in FIG. 6B could have its own bypass circuit BF to bypass its then conditioning circuit, all in the manner as described above in relation to FIGS. 1-3 for example.

Figure 7:
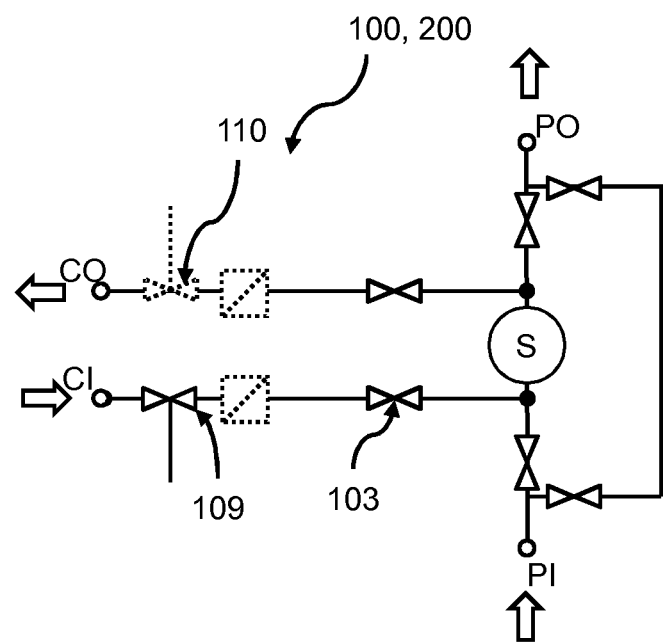
FIG. 7 shows an embodiment with a ventilator according to one or more embodiments of the present disclosure.

FIG. 7 shows an embodiment with a ventilator according to one or more embodiments of the present disclosure. In one embodiment, the fluid paths PF, BF, CF are comprised in the fluid sensor arrangement 100 or in the sensor unit 200. The sensor arrangement according to any of the preceding claims, wherein the bypass fluid path BF further comprises a first ventilator 109 and/or a second ventilator 110. The ventilator may be provided as a valve, a bubble trap or a bag receiving air. The ventilator may also be provided with a sterile filter in case that air is to be released into atmosphere.

Embodiments with a ventilator provide the advantage that air can be eliminated from the conditioning path CF for example if the sensor shall be protected from air or air cannot or shall not be introduced downstream the sensor or the sensor arrangement.

Figure 8:
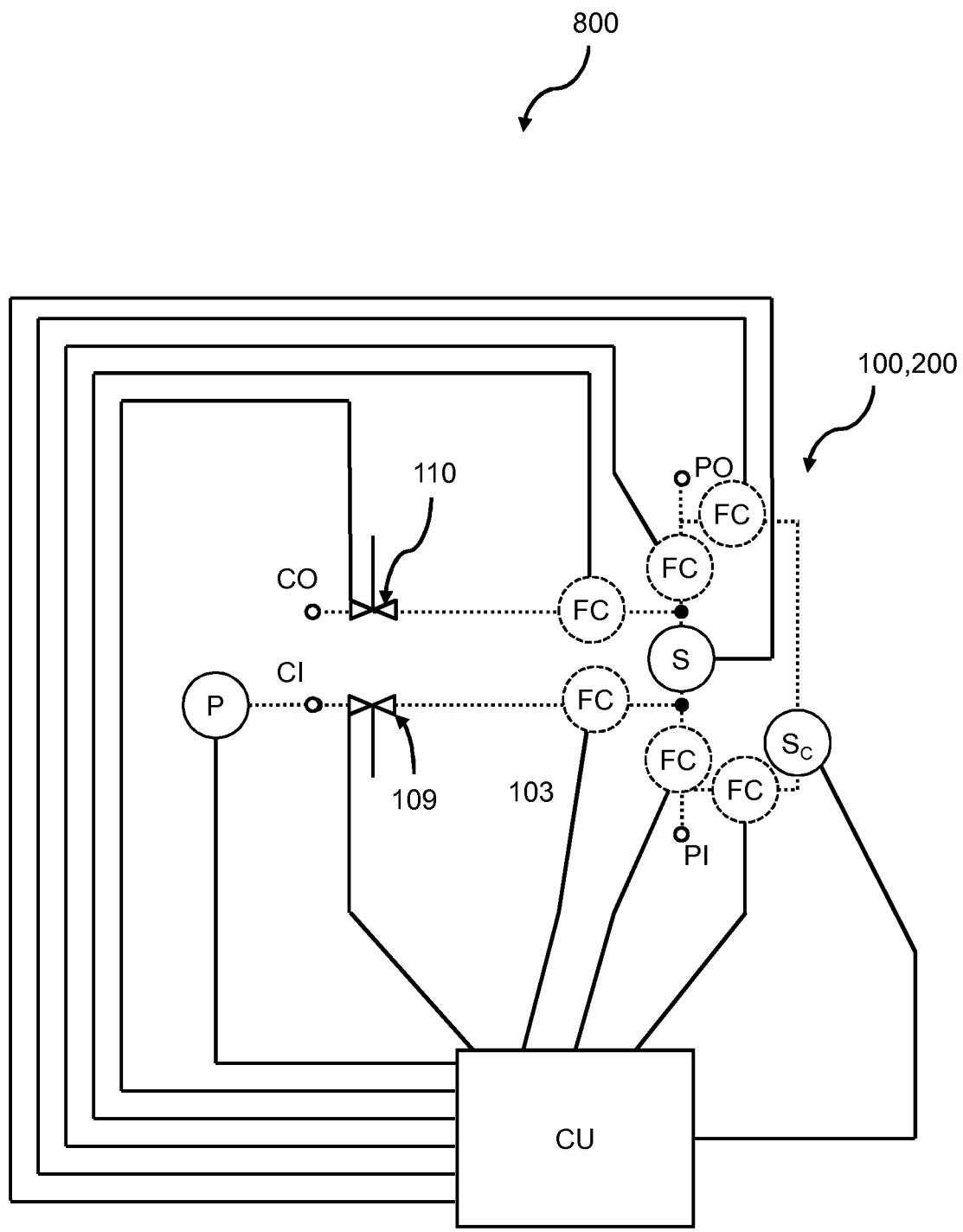
FIG. 8 shows a bioprocessing sensor system according to one or more embodiments of the present disclosure.

FIG. 8 shows a bioprocessing sensor system 800 according to one or more embodiments of the present disclosure. In one embodiment, a bioprocessing sensor system 800 configured for aseptic sensor S conditioning is provided. The system 800 comprises a control unit CU and a sensor arrangement 100 or a sensor unit 200. The control unit CU is configured to perform any of the method steps described herein.

In one embodiment, and as further described in relation to FIG. 1-7, the sensor arrangement 100 or a sensor unit 200 may further comprise a selection of any of one or more flow controls FC. In one embodiment, the flow controls FC, e.g. valves, of the sensor arrangement 100 or the sensor unit 200 are communicatively coupled to the control unit CU. The valves ventilators and configured to operate in an operational mode or to operate in a conditioning mode in response to control signals received from the control unit CU.

In one embodiment, the sensors S, $S_c$, e.g. PH sensors, of the sensor arrangement 100 or the sensor unit 200 are communicatively coupled to the control unit CU. The sensors are configured to measure process properties/variables of the process fluid and send control signals comprising the measured process properties/variables to the control unit CU.

In one embodiment, the sensors ventilators 109, 110, of the sensor arrangement 100 or the sensor unit 200 are communicatively coupled to the control unit CU. The sensors may be configured to be activated and let air out of the conditioning fluid path and/or configured to be deactivated and not let air out of the conditioning fluid path in response to control signals received from the control unit CU.

As further described in relation to FIG. 1-7, the sensor arrangement 100 or a sensor unit 200 may further comprise process the fluid inlet/outlet PI, PO, and conditioning fluid inlet/outlet CI, CO. Optionally the bioprocessing sensor system 800 may further comprise a fluid source P, such as a pump, coupled/connected to the conditioning fluid inlet and being communicatively coupled to the control unit CU.

In one example, an optional pump P is added upstream the inlet CI and connected to the control unit CU. The pump can be operated manually by a user or automated and controlled by the control unit via control signals. An example for a manual pump could be a syringe type of pump unit with manual valves or check valves for prescribing the direction of flow. In another example, the pump is automated and connected to the control unit CU. The automated pump may be any one of may be a peristaltic pump, a piston pump or a diaphragm pump. The wetted parts of the pump, for example a syringe or a pump tube for a peristaltic pump, may be provided as a consumable. In one embodiment, the wetted parts of the pump are provided as pre-sterilized components and the pump is connected aseptically to the conditioning fluid inlet CI using an aseptic connector. The aseptic connector may be a multi-connector allowing multiple aseptic connection and disconnection. Conditioning fluid may be connected or pre-connected aseptically upstream the pump.

Figure 9:
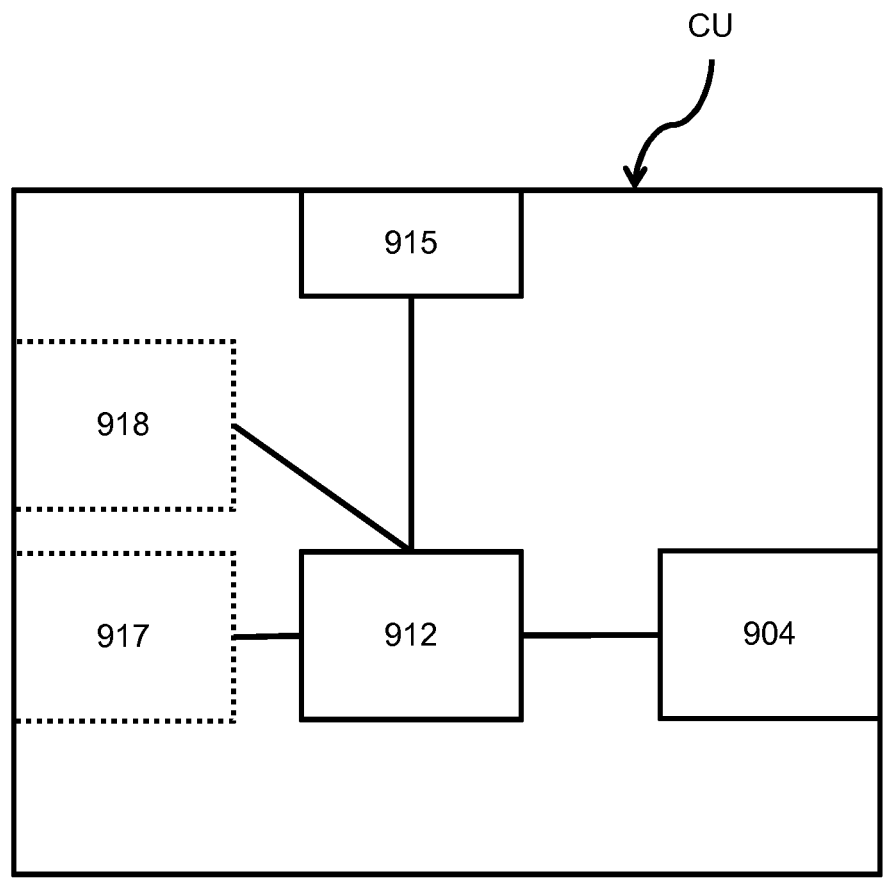
FIG. 9 shows the control unit according to one or more embodiments of the present disclosure.

FIG. 9 shows the control unit CU according to one or more embodiments of the present disclosure. The control unit CU may be in the form of e.g. an Electronic Control unit, a server, an on-board control unit, a stationary computing device, a laptop control unit, a tablet control unit, a handheld control unit, a wrist-worn control unit, a smart watch, a smartphone or a smart TV. The control unit CU may comprise processing circuitry 912 communicatively coupled to a communications interface, e.g. a transceiver 904, configured for wired or wireless communication. The control unit CU may further comprise at least one optional antenna (not shown in figure). The antenna may be coupled to the transceiver 904 and is configured to transmit and/or emit and/or receive wired or wireless signals in a communication network, such as WiFi, Bluetooth, 3G, 4G, 5G etc. In one example, the processing circuitry 912 may be any of a selection of a processor and/or a central processing unit and/or processor modules and/or multiple processors configured to cooperate with each-other. Further, the control unit CU may further comprise a memory 915 communicatively coupled to the processing circuitry 912. The memory 915 may e.g. comprise a selection of a hard RAM, disk drive, a floppy disk drive, a flash drive or other removable or fixed media drive or any other suitable memory known in the art. The memory 915 may contain instructions executable by the processing circuitry to perform any of the steps or methods described herein. The processing circuitry 912 may be communicatively coupled to a selection of any of the transceiver 904 and the memory 915.

The control unit CU may be configured to send/receive control signals directly to/from any of the above mentioned units or to external nodes or to send/receive control signals via a wired and/or wireless communications network.

The wired/wireless transceiver 904 and/or a wired/wireless communications interface may be configured to send and/or receive data values or parameters as a signal to or from the processing circuitry 912 to or from other external nodes.

In an embodiment, the transceiver 904 communicates directly to external nodes or via the wireless communications network.

In one or more embodiments the control unit CU may further comprise an input device 917, configured to receive input or indications from a user and send a user input signal indicative of the user input or indications to the processing circuitry 912.

In one or more embodiments the control unit CU may further comprise a display 918 configured to receive a display signal indicative of rendered objects, such as text or graphical user input objects, from the processing circuitry 912 and to display the received signal as objects, such as text or graphical user input objects.

In one embodiment the display 918 is integrated with the user input device 917 and is configured to receive a display signal indicative of rendered objects, such as text or graphical user input objects, from the processing circuitry 912 and to display the received signal as objects, such as text or graphical user input objects, and/or configured to receive input or indications from a user and send a user-input signal indicative of the user input or indications to the processing circuitry 912.

In a further embodiment, the control unit CU may further comprise and/or be coupled to one or more additional sensors (not shown in the figure) configured to receive and/or obtain and/or measure physical properties pertaining to the bioprocessing system 800 and send one or more sensor signals indicative of the physical properties to the processing circuitry 912. An example of such an additional sensor may be an ambient air pressure sensor configured to measure the ambient air pressure where the bioprocessing system 800 is located.

In one or more embodiments, the processing circuitry 912 is further communicatively coupled to the input device 917 and/or the display 918 and/or the additional sensors.

In embodiments, the communications network communicate using wired or wireless communication techniques that may include at least one of a Local Area Network (LAN), Metropolitan Area Network (MAN), Global System for Mobile Network (GSM), Enhanced Data GSM Environment (EDGE), Universal Mobile Telecommunications System, Long term evolution, High Speed Downlink Packet Access (HSDPA), Wideband Code Division Multiple Access (W-CDMA), Code Division Multiple Access (CDMA), Time Division Multiple Access (TDMA), Bluetooth®, Zigbee®, Wi-Fi, Voice over Internet Protocol (VoIP), LTE Advanced, IEEE802.16m, WirelessMAN-Advanced, Evolved High-Speed Packet Access (HSPA+), 3GPP Long Term Evolution (LTE), Mobile WiMAX (IEEE 802.16e), Ultra Mobile Broadband (UMB) (formerly Evolution-Data Optimized (EV-DO) Rev. C), Fast Low-latency Access with Seamless Handoff Orthogonal Frequency Division Multiplexing (Flash-OFDM), High Capacity Spatial Division Multiple Access (iBurst®) and Mobile Broadband Wireless Access (MBWA) (IEEE 802.20) systems, High Performance Radio Metropolitan Area Network (HIPERMAN), Beam-Division Multiple Access (BDMA), World Interoperability for Microwave Access (Wi-MAX) and ultrasonic communication, etc., but is not limited thereto.

Moreover, it is realized by the skilled person that the control unit CU may comprise the necessary communication capabilities in the form of e.g., functions, means, units, elements, etc., for performing the present solution. Examples of other such means, units, elements and functions are: processors, memory, buffers, control logic, encoders, decoders, rate matchers, de-rate matchers, mapping units, multipliers, decision units, selecting units, switches, interleavers, de-interleavers, modulators, demodulators, inputs, outputs, antennas, amplifiers, receiver units, transmitter units, DSPs, MSDs, TCM encoder, TCM decoder, power supply units, power feeders, communication interfaces, communication protocols, etc. which are suitably arranged together for performing the present solution.

Especially, the processing circuitry of the present disclosure may comprise one or more instances of a processor, processor modules and multiple processors configured to cooperate with each-other, Central Processing Unit (CPU), a processing unit, a processing circuit, a processor, an Application Specific Integrated Circuit (ASIC), a microprocessor, a Field-Programmable Gate Array (FPGA) or other processing logic that may interpret and execute instructions. The expression "processing circuitry" and/or "processing means" may thus represent a processing circuitry comprising a plurality of processing circuits, such as, e.g., any, some or all of the ones mentioned above. The processing means may further perform data processing functions for inputting, outputting, and processing of data comprising data buffering and device control functions, such as call processing control, user interface control, or the like.

Figure 10:
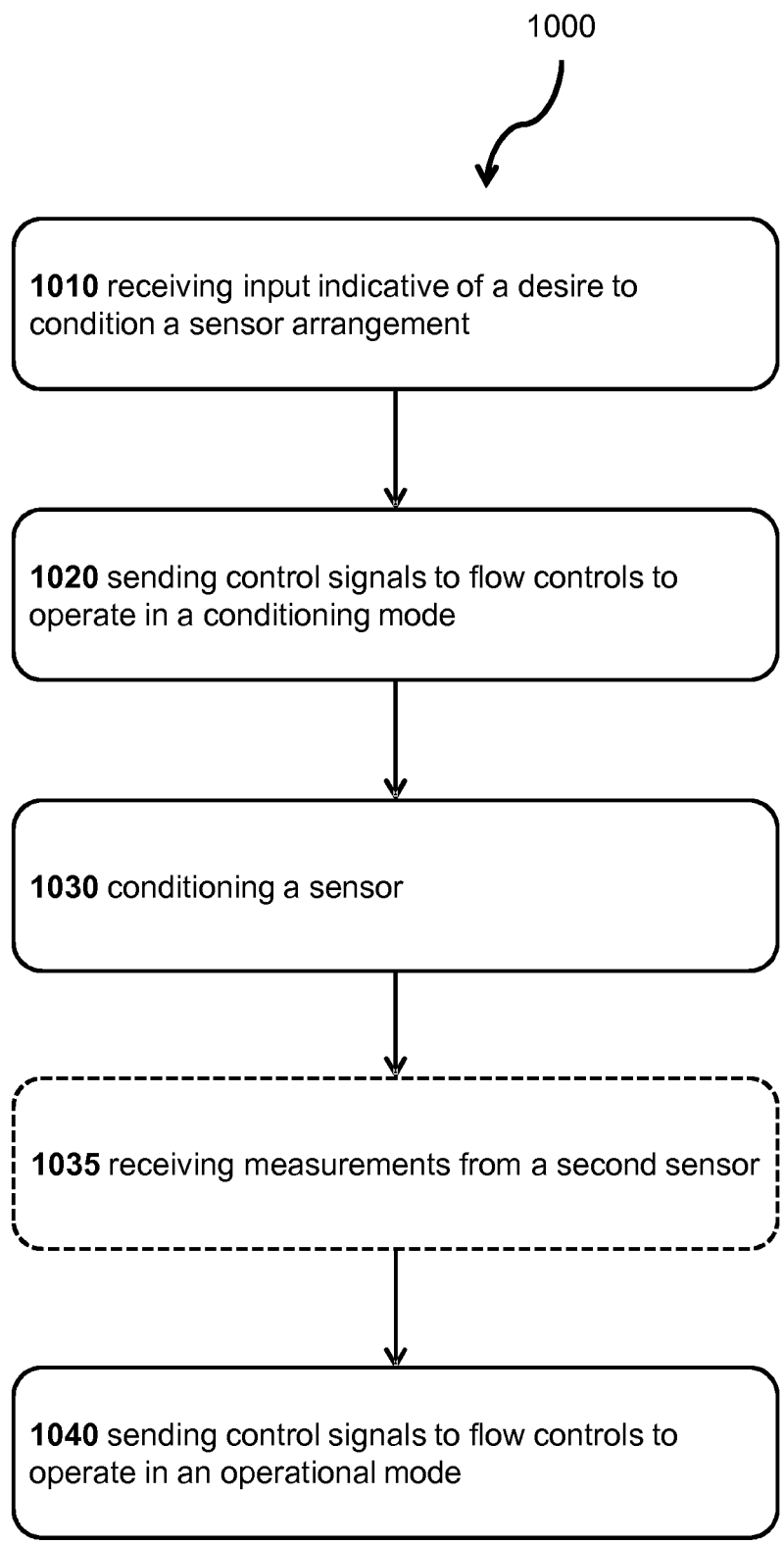
FIG. 10 shows a flowchart of a method according to one or more embodiments of the present disclosure.

FIG. 10 shows a flowchart of a method 1000 according to one or more embodiments of the present disclosure. A method 10000 is provided and performed by a bioprocessing sensor system 1000 configured for aseptic sensor S conditioning, the method comprising:

Step 1010: receiving input indicative of a desire to condition the sensor arrangement 100 or the sensor unit 200 of the bioprocessing sensor system 1000. The input may be provided by a user of the system 800 via the input device 917 or as a control signal from an external node.

In one example, the continuous bioprocessing system 800 is normally operating in an operational mode. When a certain conditioning requirement is fulfilled, e.g. operating the bioprocessing system 800 for a certain number of hours triggers the need for calibration of the sensor S, Step 1020: sending control signals from a control unit CU to one or more of the flow controls FC, thereby indicating to the flow controls FC to operate in a conditioning mode. Operation in a conditioning mode is further described in relation to FIG. 2 and FIG. 3.

Step 1030: conditioning a sensor S. Conditioning the sensor may involve any selection of any of calibration of the sensor, cleaning of the sensor, regenerating the sensor and storing or replacing the sensor. In one embodiment, conditioning the sensor S comprises calibrating the sensor S by receiving measurements of process properties/variables from the sensor S, and calculating calibration parameters using the received measurements and historical calibration parameters. The calculated calibration parameters may then be stored in memory and later used to correct or compensate measured process properties/variables.

More specifically, the sensor may be contacted with one or more calibration fluids in a condition step. Alternatively, the sensor may be controlled for functionality or accuracy in a conditioning step by contact with a known solution without performing a re-calibration. Alternatively, the sensor may be cleaned or regenerated in a conditioning step. In another example, the sensor may be aseptically disconnected in order to aseptically connect a new or a different sensor, for example a sensor measuring a different parameter or measuring the same parameter in a different range. Other conditioning such as calibrating, checking functionality or accuracy may follow the installation of a new sensor. In one example, a newly installed sensor may require a conditioning for activation of the sensor before use, for example wetting under certain incubation conditions for time or fluid. An example for the latter is a single-use pH electrode that is stored and installed in dry state prior to use.

In an optional embodiment, further described in relation to FIG. 6A and FIG. 6B, the method further comprises receiving measurements from a second sensor $S_c$.

In one example, the sensor arrangement 100 or the sensor unit 200 is operating in conditioning mode. Conditioning fluid is flowing from the fluid inlet CI to the fluid outlet CO through a conditioning fluid path CF and via the sensor S. Process fluid is simultaneously flowing from the process fluid inlet PI to the process fluid outlet PO through the process fluid path CF via the second sensor $S_c$, e.g. via an inlet and outlet of the second sensor $S_c$. Measurements of process properties/variables may then, in the conditioning mode, be received from the second sensor $S_c$.

Step 1040: sending control signals from the control unit CU to the one or more of the flow controls FC, thereby indicating to the flow controls FC to operate in the operational mode.

Measurements of process properties/variables may then again, in the operational mode, be received from the sensor S.

Finally, it should be understood that the invention is not limited to the embodiments described above, but also relates to and incorporates all embodiments within the scope of the appended independent claims.

The invention claimed is:

1. A bioprocessing fluid sensor arrangement for sensing fluidic properties in a process fluid path with a sensor, configured for aseptically connecting the sensor with at least one conditioning fluid while separating said sensor from the process fluid to at least one conditioning fluid e.g. for calibration, cleaning, regenerating and/or storing the sensor, the arrangement comprising:
   a process fluid path having a process fluid inlet and a process fluid outlet;

a sensor arranged in the process fluid path;
a bypass fluid path in the process fluid path, for bypassing the sensor, comprising a bypass inlet and a bypass outlet, one on each side of the sensor;
a conditioning or cleaning fluid path having an inlet and an outlet each aseptically and fluidically connected to the process fluid path, one on each side of the sensor, and each positioned between the bypass inlet and the bypass outlet;
and flow controls comprising a processor programmed for controlling the flow of fluids, whereby fluids can be controlled to flow in each of a) the process fluid path via the sensor, b) the bypass fluid path omitting the sensor from the fluid path, and c) the conditioning or cleaning fluid path including the sensor in said flow but omitting other portions of the process fluid path and bypass fluid path.

2. The sensor arrangement according to claim 1, wherein:
the bypass fluid path comprises flow controls in the form of a bypass inlet valve coupled to the process fluid inlet and an inlet of the sensor,
the process fluid path comprises flow controls in the form of a process fluid inlet valve coupled between the process fluid inlet and the inlet of the sensor and a process fluid outlet valve coupled between an outlet of the sensor and the process fluid outlet,
the conditioning or cleaning fluid path comprises flow controls in the form of a conditioning fluid inlet valve and a conditioning fluid outlet valve,
wherein the conditioning fluid inlet valve, the conditioning fluid outlet valve and the bypass inlet valve are configured to stop fluid to flow through the valves or to allow fluid to flow through the valves, and
wherein the process fluid inlet valve and the process fluid outlet valve are configured to allow fluid to flow through the valves or configured to stop fluid to flow through the valves.

3. The sensor arrangement according to claim 1, wherein the conditioning or cleaning fluid path further comprises a first sterile filter.

4. The sensor arrangement according to claim 1, further comprising a second sensor, the second sensor:
being arranged in the process fluid path, or
being arranged in the bypass fluid path.

5. The sensor arrangement according to claim 1, wherein the bypass fluid path further comprises a first ventilator.

6. The sensor arrangement according to claim 1, wherein a bypass fluid path of the internal coupling network further comprises a first sterile filter.

7. The sensor arrangement according to claim 1, further comprising a second sensor of the same type as the sensor, the second sensor:
being arranged in a process fluid path, or being arranged in a bypass fluid path.

8. The sensor arrangement according to claim 1, wherein a bypass fluid path of the internal coupling network further comprises a first ventilator.

9. A bioprocessing sensor system configured for aseptic sensor conditioning, the system comprising:
a processor, and
a sensor arrangement according to claim 1, wherein flow controls and sensors of a coupling network of the sensor arrangement are communicatively coupled to the control unit and configured to operate in an operational mode or to operate in a conditioning mode in response to control signals received from the processor.

10. A method performed by a bioprocessing sensor system configured for aseptic sensor conditioning, the method comprising:
receiving input indicative of a desire to condition the sensor arrangement according to claim 1,
sending control signals from a processor to one or more flow controls indicating to the flow controls to operate in a conditioning mode,
conditioning a sensor,
sending control signals from the control unit to the one or more flow controls of the sensor arrangement or the sensor unit indicating to the valves to operate in an operational mode.

11. The method of claim 10, further comprising receiving measurements from a second sensor when operating in the conditioning mode.

12. A bioprocessing sensor unit for sensing fluidic properties in a process fluid path and further configured for aseptic sensor connection to additional conditioning or cleaning or bypass fluid paths, comprising:
a body,
process couplers, coupled to the body and configured to provide aseptic connection via a process fluid inlet and a process fluid outlet of the sensor unit,
a bypass inlet and a bypass outlet positioned one on each side of the sensor unit,
conditioning couplers coupled to the body and configured to provide aseptic connection via a conditioning fluid inlet and a conditioning fluid outlet of the sensor unit, the conditioning fluid inlet and the conditioning fluid outlet positions one on each side of the sensor unit and each positions between the bypass inlet and the bypass outlet,
an internal coupling network comprising fluid paths and one or more flow controls comprising a processor programmed for controlling the flow of fluids in the fluid paths, the internal coupling network configured to operate in each of:
a) an operational mode, where the flow controls of the internal coupling network are configured to allow fluid to flow from the process fluid inlet to the process fluid outlet via a sensor, and
b) a conditioning mode, where the flow controls of the internal coupling network are configured to allow fluid to flow from the conditioning fluid inlet to the conditioning fluid outlet via the sensor or to flow from a calibration fluid inlet to a calibration fluid outlet via the sensor.

13. The sensor unit according to claim 12, wherein:
a bypass fluid path of the internal coupling network comprises a bypass inlet valve coupled to the process fluid inlet and an inlet of the sensor,
a process fluid path of the internal coupling network comprises a process fluid inlet valve coupled between the process fluid inlet and the inlet of the sensor and a process fluid outlet valve coupled between an outlet of the sensor and the process fluid outlet,
a conditioning or cleaning fluid path of the internal coupling network comprises a conditioning fluid inlet valve and a conditioning fluid outlet valve,
wherein the conditioning fluid inlet valve, the conditioning fluid outlet valve and the bypass inlet valve are configured to stop fluid to flow through the valves in the operational mode and configured to allow fluid to flow through the valves in the conditioning mode, and
wherein the process fluid inlet valve and the process fluid outlet valve are configured to allow fluid to flow through the valves in the operational mode and configured to stop fluid to flow through the valves in the conditioning mode.

14. A processor programmed to execute instructions stored on a non-transitory computer-readable memory for causing a sensor arrangement; where the instructions are executed by the processor comprised in the sensor arrangement, to perform the method steps of claim 1.

15. A non-transitory computer-readable medium having stored thereon computer executable instructions having the program according to claim 14 embodied therein.

\* \* \* \* \*